United States Patent
Kato

(10) Patent No.: US 8,360,639 B2
(45) Date of Patent: Jan. 29, 2013

(54) RADIATION IMAGING SYSTEM AND ASSIST APPARATUS FOR THE SAME

(75) Inventor: Kenichi Kato, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 287 days.

(21) Appl. No.: 12/926,937

(22) Filed: Dec. 20, 2010

(65) Prior Publication Data

US 2011/0150179 A1      Jun. 23, 2011

(30) Foreign Application Priority Data

Dec. 22, 2009   (JP) ................................ 2009-290285

(51) Int. Cl.
*H05G 1/02* (2006.01)
*G01N 23/04* (2006.01)
(52) U.S. Cl. ......................................... 378/197; 378/62
(58) Field of Classification Search ............... 378/62, 378/98.8, 193–197; 250/393, 370.08
See application file for complete search history.

(56) References Cited

U.S. PATENT DOCUMENTS

| 5,485,500 | A | 1/1996 | Baba et al. |
| 6,200,024 | B1 * | 3/2001 | Negrelli ........................ 378/197 |
| 6,325,537 | B1 * | 12/2001 | Watanabe ..................... 378/197 |
| 6,940,948 | B1 * | 9/2005 | Tretiakov et al. ............. 378/146 |
| 2010/0074505 | A1 * | 3/2010 | Oogami ........................ 382/132 |
| 2011/0064193 | A1 * | 3/2011 | Minnigh et al. ................ 378/62 |

FOREIGN PATENT DOCUMENTS

JP   2005-270277   10/2005

* cited by examiner

*Primary Examiner* — Irakli Kiknadze
(74) *Attorney, Agent, or Firm* — Jean C. Edwards, Esq; Edwards Neils PLLC

(57) ABSTRACT

In an X ray imaging system, a rotational support device supports an X ray source in a rotatable manner, to adjust an orientation angle thereof. An angle detector is disposed on the X ray source removably, for detecting the orientation angle. A shift determiner operates when the X ray source is moved pivotally, and determines a shift amount for an FPD device to a position opposed to the X ray source according to the orientation angle from the angle detector and a distance between the X ray source and the FPD device. A pseudo signal generator generates a pseudo signal of a level irrespective of the shift amount by correcting a detection signal from a shift detector according to the shift amount from the shift determiner, and supplies a second moving device with the pseudo signal. Movement of the FPD device is controlled according to the shift amount.

15 Claims, 9 Drawing Sheets

F I G. 10
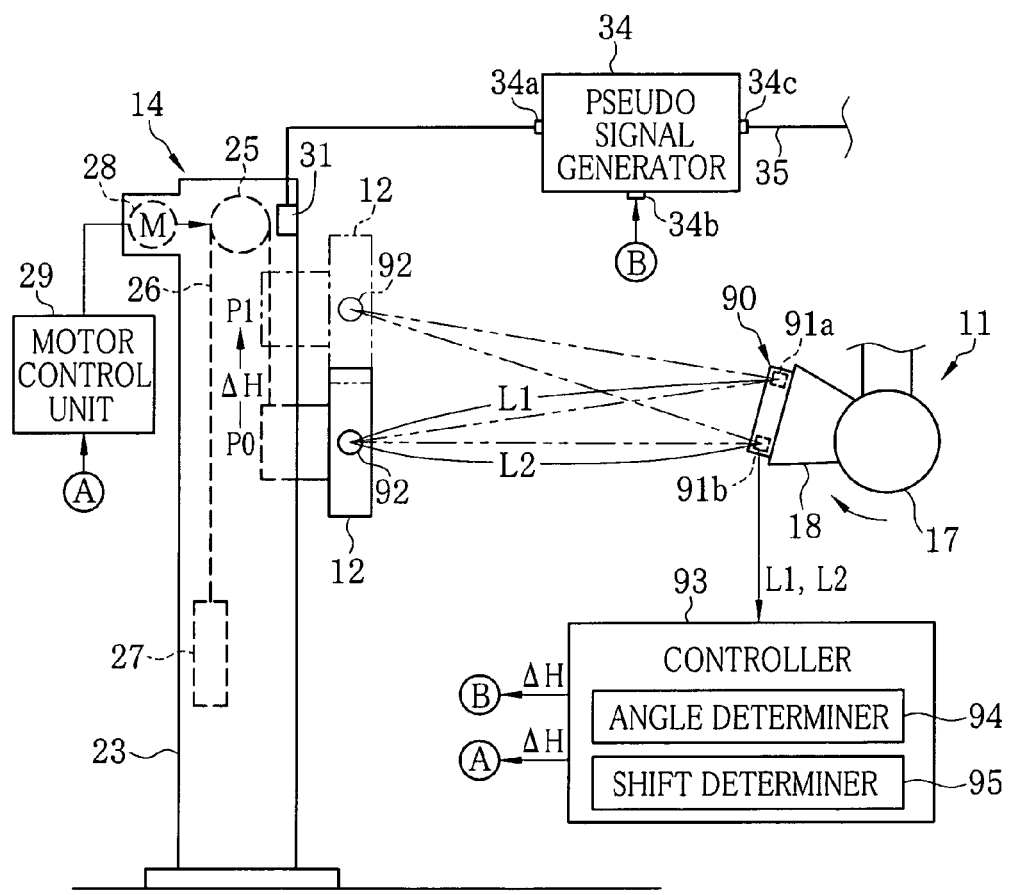

RADIATION IMAGING SYSTEM AND ASSIST APPARATUS FOR THE SAME

CROSS-REFERENCE TO RELATED APPLICATIONS

The present application claims priority from Japanese Patent Application No. 2009-290285, filed Dec. 22, 2009, the contents of which are herein incorporated by reference in their entirety.

BACKGROUND OF THE INVENTION

1. Field of the Invention

The present invention relates to a radiation imaging system and assist apparatus for the same. More particularly, the present invention relates to a radiation imaging system in which radiation from a radiation apparatus is detected by a radiation detection apparatus for imaging of a body, and an angle of the radiation apparatus can be precisely controlled, and assist apparatus for the same.

2. Description Related to the Prior Art

Long region imaging or image production for a large area image is known and used in medical imaging to observe an area of a full spine or full leg of a body of a patient, mainly in order to measure various bones. The use of a long imaging plate cassette (IP cassette) and a long film is known as a radiation detection apparatus. A distance (SID or source image distance) from an X ray source or radiation source to the radiation detection apparatus is determined as a large value to cover the entire area of imaging. This is effective in forming a long region image or stitched image only by one operation of imaging.

An FPD device (flat panel detector) as radiation detection device has been widely used as one example of the radiation detection apparatus, and receives transmitted X rays or radiation and converts this directly into data of a digital image. However, it is extremely difficult to construct the FPD device in a large size in contrast with the long imaging plate cassette (IP cassette) or long film. A largest size of a known type of the FPD device is 17 inches×17 inches. JP-A 2005-270277 discloses a technique for the long region imaging of the full spine or full leg even by use of the FPD device. An entire area of imaging is split in plural element areas of image positions, in which the body is imaged for plural times. Component images are formed from the image positions, and combined to form the long region image by image stitching.

In the long region imaging with the FPD device, it is necessary to move the X ray source by following the motion of the FPD device for radiation or X rays from the X ray source to become exactly incident on a detection area on the FPD device. Two types of mechanisms for moving the X ray source are known, including a translational motion mechanism and a rotational motion mechanism. The translational motion mechanism moves the X ray source linearly in response to motion of the FPD device. The rotational motion mechanism changes the angle of the X ray source to change an angle of the radiation or X rays in response to the motion of the FPD device.

It has been known that the rotational motion mechanism is more preferable than the translational motion mechanism for the reason of image stitching of component images of adjacent ones of the image positions. See U.S. Pat. No. 5,485,500 (corresponding to JP-A 7-059764). This is because the radiation incident upon the FPD device is not parallel beams but diffusive beams which initially travel from a focal point of the X ray source. In the translational motion mechanism, positions of focusing of the radiation are different between the image positions. There is a difference in an incident angle of the radiation between the component images within overlapping regions between adjacent ones of the component images. There occurs a problem in low precision in the matching of the component images in the overlapping regions. The long region image from the translational motion mechanism has a low quality in the continuous property between the component images in the overlapping regions. In contrast, in the rotational motion mechanism, a focal point of the radiation is fixed. An angle of the radiation is only changed. No difference occurs in the incident angle of the radiation within the overlapping regions. The long region image will have high precision in the matching of the component images in the overlapping regions.

In the most widely available types of radiation imaging system in clinics, hospital or other medical facilities, there is no function for the long region imaging. Instead, an auto tracking function is used, in which the X ray source is linearly moved by following the position of the FPD device as designated by an operator. In the auto tracking function, a position of the FPD device is detected by a position sensor such as a potentiometer. An output from the position sensor is input to a controller for the X ray source according to an analog connection or retro connection on a signal line. The auto tracking function is possible only when an optical axis of the X ray source is horizontal.

In general, the X ray source can be adjustable manually for a change in the angle suitably for the upright posture or supine posture of a body. Even in the radiation imaging system only with the auto tracking function, the long region imaging with the rotational motion mechanism is possible by disabling the auto tracking function and by manually adjusting a position of the FPD device and a position and angle of the X ray source. However, the adjustment for each of events of forming a component image will take long time. Problems arise in that speed of radiation imaging will be low to lower efficiency, and that physical stress of the patient will increase considerably.

SUMMARY OF THE INVENTION

In view of the foregoing problems, an object of the present invention is to provide a radiation imaging system in which radiation from a radiation apparatus is detected by a radiation detection apparatus for imaging of a body, and an angle of the radiation apparatus can be precisely controlled, and assist apparatus for the same.

In order to achieve the above and other objects and advantages of this invention, an assist apparatus for a radiation imaging system is provided, the radiation imaging system including a radiation source for applying radiation to a body, a radiation detection device, opposed to the radiation source, for detecting the radiation transmitted through the body, to produce an image, a first moving device for moving the radiation detection device on a path parallel with a detector surface thereof, a shift detector for detecting a position of the radiation detection device, a second moving device for moving the radiation source linearly according to a detection signal from the shift detector, to follow movement of the radiation detection device, a rotational support device for supporting the radiation source in a rotatable manner about an axis, to adjust an orientation angle thereof. The assist apparatus includes an angle detector, disposed on the radiation source removably, for detecting the orientation angle. A shift determiner operates when the radiation source is moved pivotally with the rotational support device, and determines a shift amount for shifting the radiation detection device to a position opposed to the radiation source according to the orientation angle from the angle detector and a distance between the radiation source and the radiation detection device. A pseudo signal generator generates a pseudo signal of a level irrespective of the shift amount by correcting the detection signal from the shift detector according to the shift amount from the shift determiner, and supplies the second moving device with the pseudo signal.

The radiation source includes a beam limiting device for limiting a field of the radiation. A pair of filter rails are disposed on the beam limiting device, for securing of an additional filter for changing a characteristic of the radiation. The angle detector includes a detector portion retained on the filter rails.

The detector portion has a size variable in association with an interval between the filter rails.

The angle detector includes an acceleration sensor for detecting the orientation angle.

The angle detector includes two one-axis acceleration sensors arranged so that axial directions thereof are substantially perpendicular to one another. The shift determiner selects information of the orientation angle from one of the one-axis acceleration sensors having a higher angular resolution, to determine the shift amount.

The pseudo signal generator generates the pseudo signal by subtracting a signal value of the shift amount from a signal value of the position of the radiation detection device.

The shift detector is constituted by a potentiometer.

The angle detector includes a radio transmitter for transmitting information of the detected orientation angle to the shift determiner.

In one preferred embodiment, the angle detector includes two ultrasonic receivers for receiving an ultrasonic wave from an ultrasonic transmitter positioned on the radiation detection device, to measure distances from the ultrasonic transmitter. An angle determiner determines the orientation angle according to the distances measured by the ultrasonic receivers.

The shift amount has such a value as to move the radiation detection device on the path in a first direction defined according to a first rotational direction among two rotational directions of the radiation source with the first moving device when the radiation source is pivotally moved in the first rotational direction.

In one preferred embodiment, the radiation source is movable linearly in a first direction and a second direction reverse thereto with the second moving device. When the radiation source is pivotally moved in a first rotational direction defined according to the first direction, the second moving device moves the radiation source in the second direction.

The radiation detection device is an FPD device.

The radiation is X rays.

Also, a radiation imaging system includes a radiation source for applying radiation to a body. A radiation detection device is opposed to the radiation source, for detecting the radiation transmitted through the body, to produce an image. A first moving device moves the radiation detection device on a path parallel with a detector surface thereof. A shift detector detects a position of the radiation detection device. A second moving device moves the radiation source linearly according to a detection signal from the shift detector, to follow movement of the radiation detection device. A rotational support device supports the radiation source in a rotatable manner about an axis, to adjust an orientation angle thereof. An angle detector is disposed on the radiation source removably, for detecting the orientation angle. A shift determiner operates when the radiation source is moved pivotally with the rotational support device, determines a shift amount for shifting the radiation detection device to a position opposed to the radiation source according to the orientation angle from the angle detector and a distance between the radiation source and the radiation detection device. A pseudo signal generator generates a pseudo signal of a level irrespective of the shift amount by correcting the detection signal from the shift detector according to the shift amount from the shift determiner, and supplies the second moving device with the pseudo signal. A controller controls the first moving device according to the shift amount from the shift determiner.

In one preferred radiation imaging system, an angle detector is disposed on the radiation source removably, for detecting the orientation angle. A shift determiner operates when the radiation source is moved pivotally with the rotational support device, and determines a shift amount for shifting the radiation detection device to a position opposed to the radiation source according to the orientation angle from the angle detector and a distance between the radiation source and the radiation detection device. A pseudo signal generator generates a pseudo signal by subtracting a signal value of the shift amount from a signal value of the position according to the shift amount from the shift determiner, and supplies the second moving device with the pseudo signal.

Consequently, an angle of the radiation source can be precisely controlled, because the angle detector and the shift determiner cooperate for the fine adjustment.

BRIEF DESCRIPTION OF THE DRAWINGS

The above objects and advantages of the present invention will become more apparent from the following detailed description when read in connection with the accompanying drawings, in which:

FIG. 10 is an explanatory view in a side elevation and a block diagram illustrating another preferred angle detector in which a distance is measured ultrasonically.

DETAILED DESCRIPTION OF THE PREFERRED EMBODIMENT (S) OF THE PRESENT INVENTION

[1st Embodiment]

Figure 1:
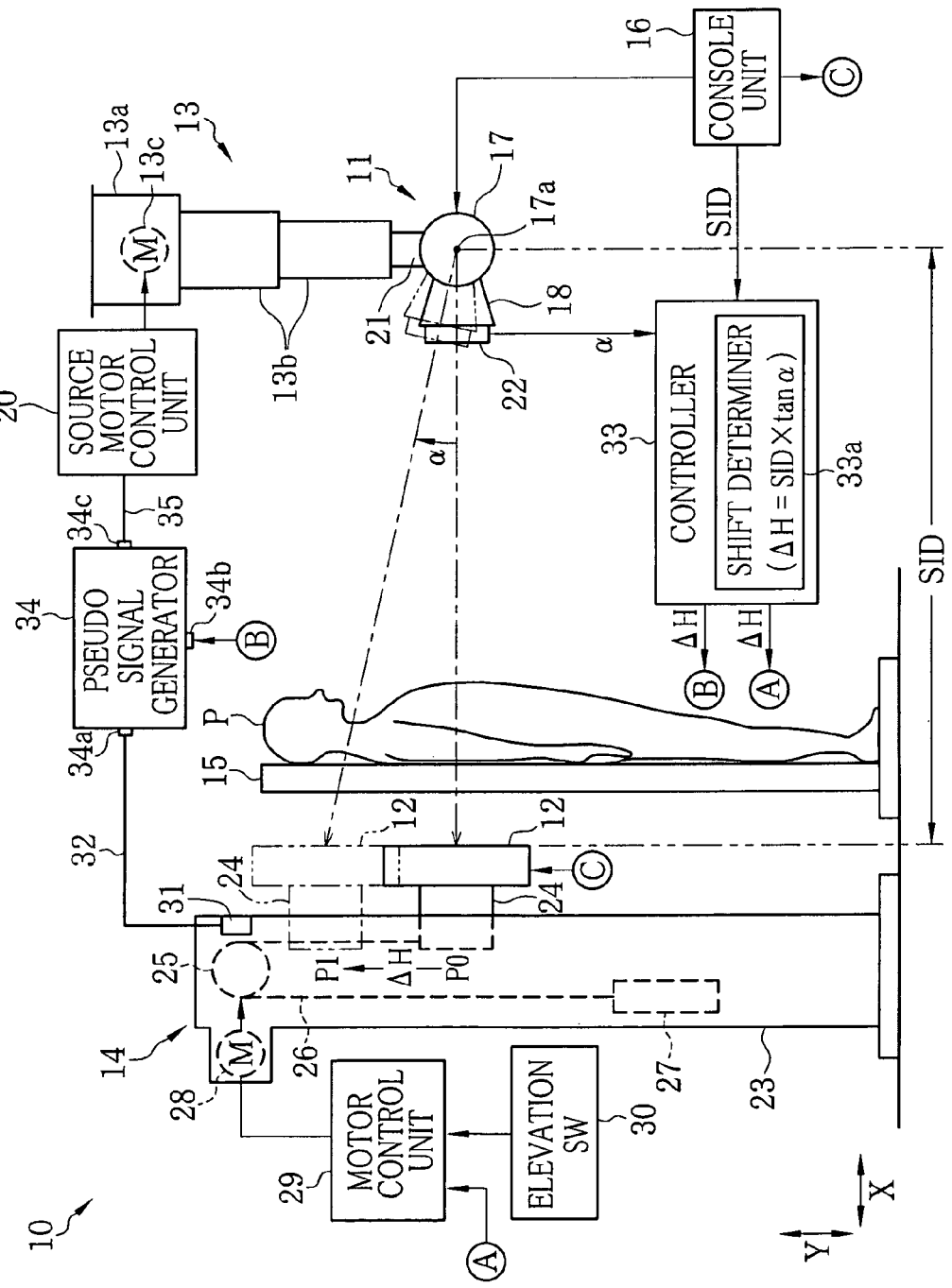
FIG. 1 is an explanatory view in a side elevation and a block diagram illustrating an X ray imaging system.

In FIG. 1, an X ray imaging system 10 or radiation imaging system is used for a body of a patient P in an upright posture.

The X ray imaging system 10 includes a radiation apparatus 13 having a support device as a second moving device, a radiation detection apparatus 14 having an elevation device as a first moving device, an upright wall 15 and a console unit 16.

An X ray source 11 is a radiation source incorporated in the radiation apparatus 13, and applies X rays to the patient P. An FPD device 12 (flat panel detector) is a radiation detection device incorporated in the radiation detection apparatus 14, detects the X rays transmitted through the patient P, and produces image data. The support device in the radiation apparatus 13 is suspended from a ceiling of a room, and supports the X ray source 11 movably up and down in a direction Y. The elevation device in the radiation detection apparatus 14 is installed on a floor, and supports the FPD device 12 movably up and down. The upright wall 15 is disposed near to the radiation detection apparatus 14 on a side of the X ray source 11, and keeps the patient P in the upright posture. The console unit 16 has an input panel, display panel and the like, and includes an imaging control device for controlling radiation of the X ray source 11 and detection of the FPD device 12 according to input signals of an operation.

The X ray source 11 includes an X ray tube 17 and a collimator 18. The X ray tube 17 generates X rays according to high voltage applied by a high voltage source (not shown). The collimator 18 as a beam limiting device absorbs unwanted components of the X rays from the X ray tube 17 for imaging of the patient P for a field of a quadrilateral shape. The X ray source 11 is controlled by an imaging control device according to manual operation of the console unit 16, and adjusted for a time sequence and dose of X rays. The collimator 18 has a movable collimator leaf for masking. Openness of the collimator leaf is adjusted by the imaging control device.

The radiation apparatus 13 includes a support housing 13a of a hanging type of radiation, and supports 13b. There are upper rails (not shown) attached to the ceiling. The support housing 13a is connected to the upper rails movably in a horizontal direction X. The supports 13b are connected to the support housing 13a in a vertical direction. A source motor 13c as a second moving device is secured to the support housing 13a for extending and compressing the supports 13b vertically by telescoping to change a position of the X ray source 11 in the vertical direction.

A source motor control unit 20 (second) controls the source motor 13c. A pseudo signal generator 34, which will be described later, generates a signal for the source motor control unit 20 to control the source motor 13c. The source motor control unit 20, though depicted outside the radiation apparatus 13 in the drawing, is contained in the support housing 13a together with the source motor 13c.

The X ray tube 17 has a pivot axis 17a or X ray focal point. A rotational support device 21 is disposed on the supports 13b of the radiation apparatus 13, and supports the X ray source 11 in a rotatable manner about the pivot axis 17a. An operator manually changes the orientation angle of the X ray source 11, to change a radiation area of X rays in a longitudinal direction or height direction of the body of the patient P or vertical direction.

Basic structures of the X ray source 11, the radiation apparatus 13 and the console unit 16 are well-known. In the embodiment, an angle detector 22 is secured to the collimator 18 of the X ray source 11 removably for detecting an orientation angle of the X ray source 11 for radiation.

The radiation detection apparatus 14 includes an elevation housing 23 of an upright type and a detector support 24. The elevation housing 23 is installed on the floor. The detector support 24 supports the FPD device 12. There is a pulley 25 about which a wire 26 extends for transmission. The wire 26 has first and second ends. The detector support 24 is secured to the first end of the wire 26. A counter weight 27 is secured to the second end for balancing with the detector support 24. A motor 28 as a first moving device rotates the pulley 25, which causes the FPD device 12 to move up and down. Note that other mechanisms can be used for the detector support 24, for example on including a pulley and an endless belt.

A motor control unit 29 (first) is connected to the motor 28. An elevation switch 30 generates a control signal when operated by an operator, for the motor control unit 29 to control the motor 28. The motor control unit 29, though depicted outside the elevation housing 23 in the drawing, is incorporated in the elevation housing 23 together with the motor 28. The elevation switch 30 is positioned on an outer surface of the elevation housing 23 suitably.

A potentiometer 31 as shift detector is disposed on the elevation housing 23, and measures a shift amount of the wire 26 to detect a position of the FPD device 12 in the vertical direction. The potentiometer 31 outputs a voltage of set position information of the FPD device 12 as an analog detection signal. A signal line or cable 32 of the elevation housing 23 is connected for outputting the position information.

In the radiation detection apparatus 14, a controller 33 inputs a command signal to the motor control unit 29 for moving the FPD device 12, which will be described later. Remaining elements of the radiation detection apparatus 14 are the same as those known in the field of medical instruments.

The FPD device 12 includes a matrix circuit board and a plurality of X ray detection elements. The matrix circuit board has a plurality of thin film transistors (TFT) arranged two-dimensionally. The X ray detection elements are disposed respectively to correspond to the thin film transistors, and generate and store electric charge according to the dose of incident X rays. When the thin film transistors are turned on, the stored charge is read. Two types of X ray detection elements are known, including a direct conversion type and an indirect conversion type, any of which can be used effectively in the invention.

The X ray detection element of the direct conversion type includes a conversion layer and a capacitor. The conversion layer contains amorphous selenium (a-Se) for directly converting X rays to electric charge. The capacitor stores the charge obtained by the conversion layer. The X ray detection element of the indirect conversion type includes a scintillator and a photo diode. The scintillator contains gadolinium oxide ($Gd_2O_3$) or cesium iodide (CsI) for converting X rays to visible light. The photo diode converts the obtained visible light into electric charge, and stores the charge. The FPD device 12 has a detector surface with a size of 17 inches×17 inches.

Also, the FPD device 12 includes a scan controller, an integrating amplifier and an A/D converter. The scan controller turns on the thin film transistors one after another by scanning of those line by line. The integrating amplifier integrates the charge output by the X ray detection elements through the thin film transistors, and converts the charge into a voltage signal. The A/D converter digitally converts the voltage signal from the integrating amplifier into image data. The imaging control device in the console unit 16 controls the FPD device 12 for driving and reading.

The controller 33 and the pseudo signal generator 34 are incorporated in the X ray imaging system 10 additionally to the various known elements, and constitute an assist apparatus of the invention. The controller 33 is connected to the console unit 16 and to the angle detector 22, and retrieves a distance SID between the X ray source 11 and the FPD device 12 or distance from the pivot axis 17a to the FPD device 12, and retrieves the orientation angle α of the X ray source 11 from the angle detector 22. A shift determiner 33a is included in the controller 33 for determining a shift amount of the FPD device 12 corresponding to the angle α.

The shift determiner 33a determines the shift amount ΔH of the FPD device 12 according to the distance SID between the X ray source 11 and the FPD device 12, and the angle α by use of Equation 1. The angle α is determined according to the reference direction (α=0) where X rays are directed horizontally and an optical axis (center line) of the X rays extends at the center of the FPD device 12. A sign of the value α is either positive or negative according to the upward or downward direction of rotation of the X ray source 11.

$$\Delta H = \text{SID} \times \tan \alpha \qquad \text{Equation 1}$$

The shift amount ΔH is according to the vertical direction and relative to the reference position P0 of the FPD device 12 where the center of the detector surface is as high as the pivot axis 17a. The shift amount ΔH from the shift determiner 33a is input to the motor control unit 29 of the radiation detection apparatus 14 as a command signal for moving the FPD device 12. The motor control unit 29 moves the FPD device 12 from the reference position P0 to a position P1 which is distant from the reference position P0 by the shift amount ΔH.

The controller 33 inputs the shift amount ΔH to the motor control unit 29 of the radiation detection apparatus 14 and to the pseudo signal generator 34 simultaneously. The pseudo signal generator 34, when the FPD device 12 is moved according to a change in the orientation angle of the X ray source 11, cancels a change in the output voltage of the potentiometer 31 with the movement of the FPD device 12 so as to output a pseudo signal of a constant voltage.

The pseudo signal generator 34 has a first input terminal 34a, a second input terminal 34b and an output terminal 34c. The signal line 32 is connected to the first input terminal 34a for inputting the output voltage of the potentiometer 31 to the pseudo signal generator 34 as set position information or detection signal. A signal line or cable (not shown) is connected to the second input terminal 34b for inputting a signal from the controller 33 in association with the shift amount ΔH to the pseudo signal generator 34. A signal line or cable 35 is connected to the output terminal 34c for sending a pseudo signal from the pseudo signal generator 34 to the source motor control unit 20 in the radiation apparatus 13.

In the known system, the potentiometer 31 is connected directly to the source motor control unit 20 by a signal line. The source motor control unit 20 moves the X ray source 11 up and down for the height of the FPD device 12 according to the output voltage of the potentiometer 31, which is referred to as auto tracking function. In the embodiment of the invention, in contrast, the potentiometer 31 is connected to the source motor control unit 20 via the pseudo signal generator 34 with the signal line or cable. The output voltage of the potentiometer 31 is converted so as to prevent the X ray source 11 from moving up and down even with movement of the FPD device 12 upon a change in the orientation angle of the X ray source 11. Note that, if the FPD device 12 is moved by use of the elevation switch 30, the shift amount ΔH is zero (0) because the FPD device 12 moves irrespective of a change in the orientation angle of the X ray source 11. The X ray source 11 moves up and down by following the FPD device 12.

Figure 2:
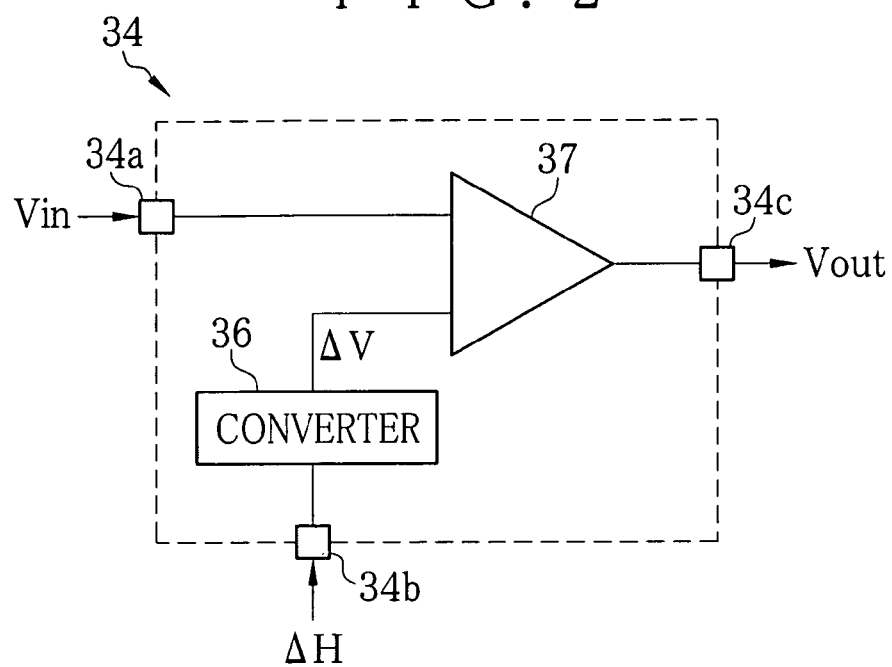
FIG. 2 is a block diagram illustrating a pseudo signal generator.

In FIG. 2, the pseudo signal generator 34 is constituted by a converter 36 and an analog arithmetic operation device 37. The converter 36 receives the signal corresponding to the shift amount ΔH from the controller 33 and converts the signal into a change amount ΔV of an output voltage generated by the potentiometer 31 upon movement of the FPD device 12 by ΔH. The analog arithmetic operation device 37 produces a pseudo signal irrespective of the shift amount ΔH by subtracting the change amount ΔV from an input voltage Vin generated by the potentiometer 31. The pseudo signal is output by way of an output voltage Vout. Note that a power source for the pseudo signal generator 34 is preferably separate from a power source for the controller 33, because the pseudo signal generator 34 is a single component in the embodiment.

Figure 3:
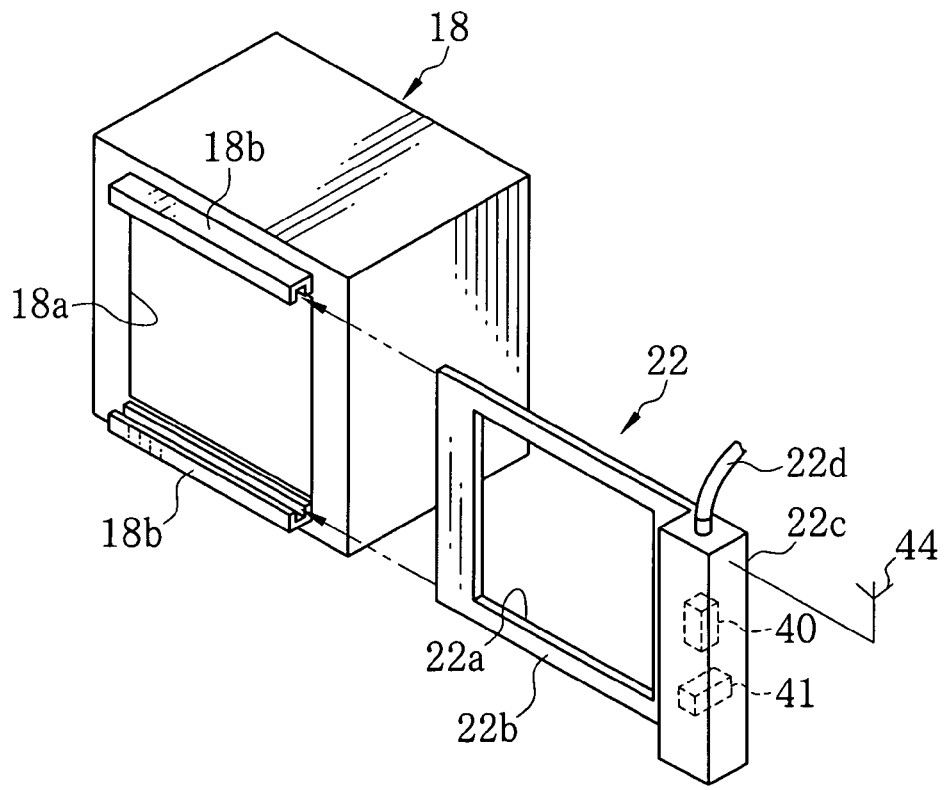
FIG. 3 is a perspective view illustrating a collimator and an angle detector.

In FIG. 3, a collimator aperture 18a is formed in the collimator 18 as a beam limiting device for X rays from the X ray tube 17. A pair of filter rails 18b are formed on portions of the collimator aperture 18a and disposed along two side lines extending horizontally. An additional filter is supported by the filter rails 18b removably for changing an X ray spectrum (radiation characteristic) according to a body part in the patient's body. The filter rails 18b are a widely used element with a collimator in well-known X ray imaging systems.

The angle detector 22 is secured to the collimator 18 by use of the filter rails 18b removably. Specifically, the angle detector 22 includes an aperture 22a, a sensor frame 22b, a sensor housing 22c and a signal line or cable 22d. The aperture 22a has a size corresponding to the collimator aperture 18a. The sensor frame 22b has a size suitable for insertion in a gap of the filter rails 18b. The sensor housing 22c is connected with the sensor frame 22b, and contains an upright posture angle sensor 40 and a supine posture angle sensor 41 or acceleration sensors. The signal line 22d outputs angle information of the angle α detected by the angle sensors 40 and 41. To the angle detector 22, power is supplied by the controller 33 through the signal line 22d. Note that the sensor frame 22b may be shaped suitably without the aperture 22a, for example, can be portions with small weight of metal of aluminum or the like.

The X ray source 11 is usable not only for imaging of the upright posture in FIG. 1 but also for imaging of the supine posture in which X rays are applied to a patient in a vertically downward direction. Thus, the angle sensors 40 and 41 are included in the angle detector 22. Each of the angle sensors 40 and 41 is a one-axis acceleration sensor, for example, acceleration sensor of an electrostatic capacity type with a semiconductor.

In general, a one-axis acceleration sensor has such a characteristic that an output voltage relative to an angle changes in a form of a sine wave, and that the angular resolution becomes the highest where its axial direction coincides with the horizontal direction, because the output voltage changes linearly relative to the change in the angle. Therefore, the angle sensors 40 and 41 are arranged with a difference of 90 degrees between their axial directions. For the imaging of the upright posture with α=0, the axial direction of the upright posture angle sensor 40 is horizontal. For the imaging of the supine posture with α=−90 degrees, the axial direction of the supine posture angle sensor 41 is horizontal. In short, an axial direction of one of the angle sensors 40 and 41 is horizontal (direction X) at the same time as the axial direction of the remaining one of those is vertical (direction Y).

Figure 4:
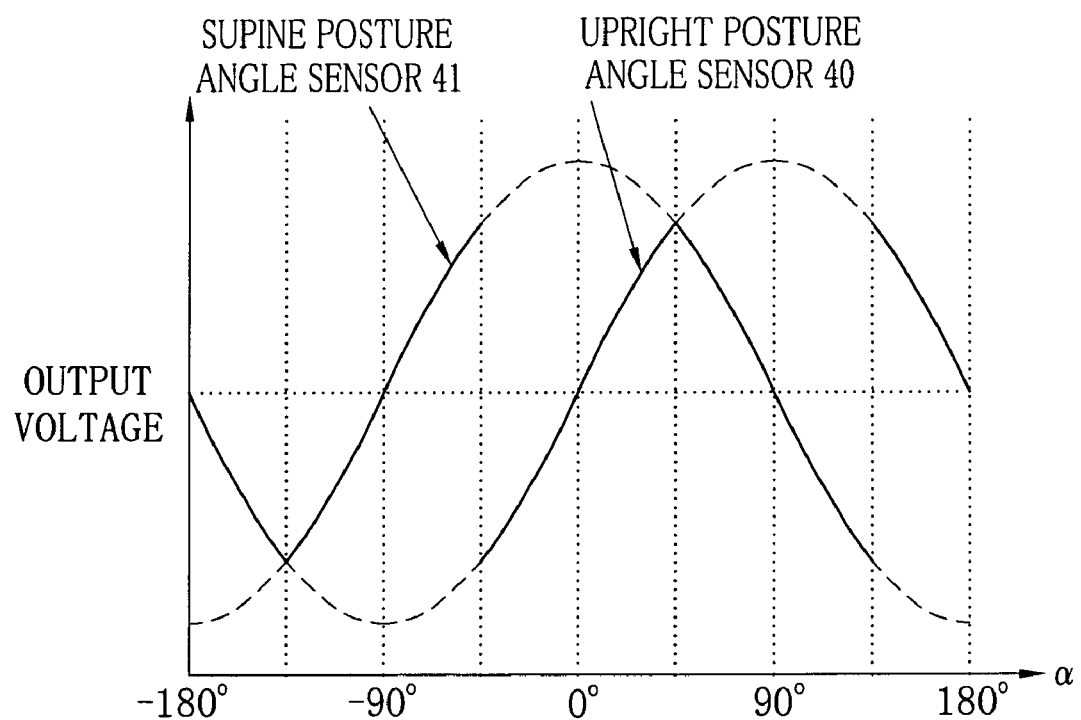
FIG. 4 is a graph illustrating an output voltage of angle sensors and an orientation angle.

In FIG. 4, output voltages of the angle sensors 40 and 41 are illustrated for the orientation angle α of the X ray source 11. Those voltages are input to the controller 33 through the signal line 22d. The controller 33 determines the angle α by use of a selected one of the voltages. The controller 33 selects the voltage from one of the angle sensors with a higher angular resolution according to the angle α in order to determine the angle α precisely in both of the upright and supine postures. In the drawing, the solid line designates the voltage selected by the controller 33.

The operation of the long region imaging of the patient P in the X ray imaging system 10 is described now. At first, an operator operates the elevation switch 30 to position the FPD device 12 substantially at the center of the area of the long region imaging, for example, position P0 of FIG. 1 as a position of a chest for an area containing the full spine. If the direction of the X ray source 11 is horizontal (α=0), then the shift amount ΔH determined by the shift determiner 33a of the controller 33 is zero (0). The pseudo signal generator 34 sends information of the output voltage from the potentiometer 31 to the source motor control unit 20. In short, Vin=Vout. The source motor 13c is driven according to the output voltage from the potentiometer 31 to move the X ray source 11 up and down for auto tracking. The X ray source 11 is positioned to set the pivot axis 17a substantially as high as the center of the FPD device 12. The operator operates the console unit 16 to form a first image.

For a second image, the operator manually moves the X ray source 11 to change the orientation angle up or down. The angle α of the X ray source 11 is detected by constant monitoring of the angle detector 22, and is input to the controller 33. The shift determiner 33a in the controller 33 determines the shift amount ΔH according to the angle α to move the FPD device 12. The obtained shift amount ΔH is output to the motor control unit 29 and the pseudo signal generator 34. As a result, the motor control unit 29 moves the FPD device 12 to a position P1 on a straight line extending in a forward direction of the X ray source 11 in FIG. 1. The voltage of the potentiometer 31 changes according to the movement of the FPD device 12. The pseudo signal generator 34 cancels the change in the voltage. A pseudo signal of a constant voltage is input to the source motor control unit 20. Thus, the X ray source 11 remains without shift. The operator operates the console unit 16 to form a second image.

Then the operator changes the direction of the X ray source 11 similarly. Third and further images are formed until the long region imaging of image stitching is completed. In conclusion, the controller 33 and the pseudo signal generator 34 are added as assist apparatus to the known X ray imaging system according to the embodiment, so as to enable the long region imaging with the rotational motion mechanism.

In the present embodiment, the angle sensors in the angle detector 22 are two one-axis acceleration sensors. However, a sensor element in the angle detector 22 can be one two-axis acceleration sensor. An example of angle sensor may be not only an acceleration sensor but an inclination sensor. It is preferable for the angle sensor for have angular resolution of an angle equal to or less than 0.3 degrees.

In the above embodiment, the signal line 22d is used for transmitting the angle information from the angle detector 22. Furthermore, a radio transmitter having an antenna 44 and a battery may be incorporated in the angle detector 22. The angle information can be wirelessly transmitted from the angle detector 22 to the controller.

In the above embodiment, the potentiometer 31 detects the position of the FPD device 12 to generate a detection signal. However, a position sensor for the FPD device 12 may be constituted by a linear encoder, rotary encoder and the like.

In the above embodiment, the distance SID is stored in the console unit 16 and is read and sent to the controller 33. Alternatively, a distance sensor can be added for measuring the distance SID between the X ray source 11 and the FPD device 12. The controller 33 can be supplied with information of the distance SID by the distance sensor.

In the above embodiment, the pseudo signal generator 34 is separate from the controller 33. However, a single unit can be constructed to include the controller 33 and the pseudo signal generator 34.

[2nd Embodiment]

Figure 5:
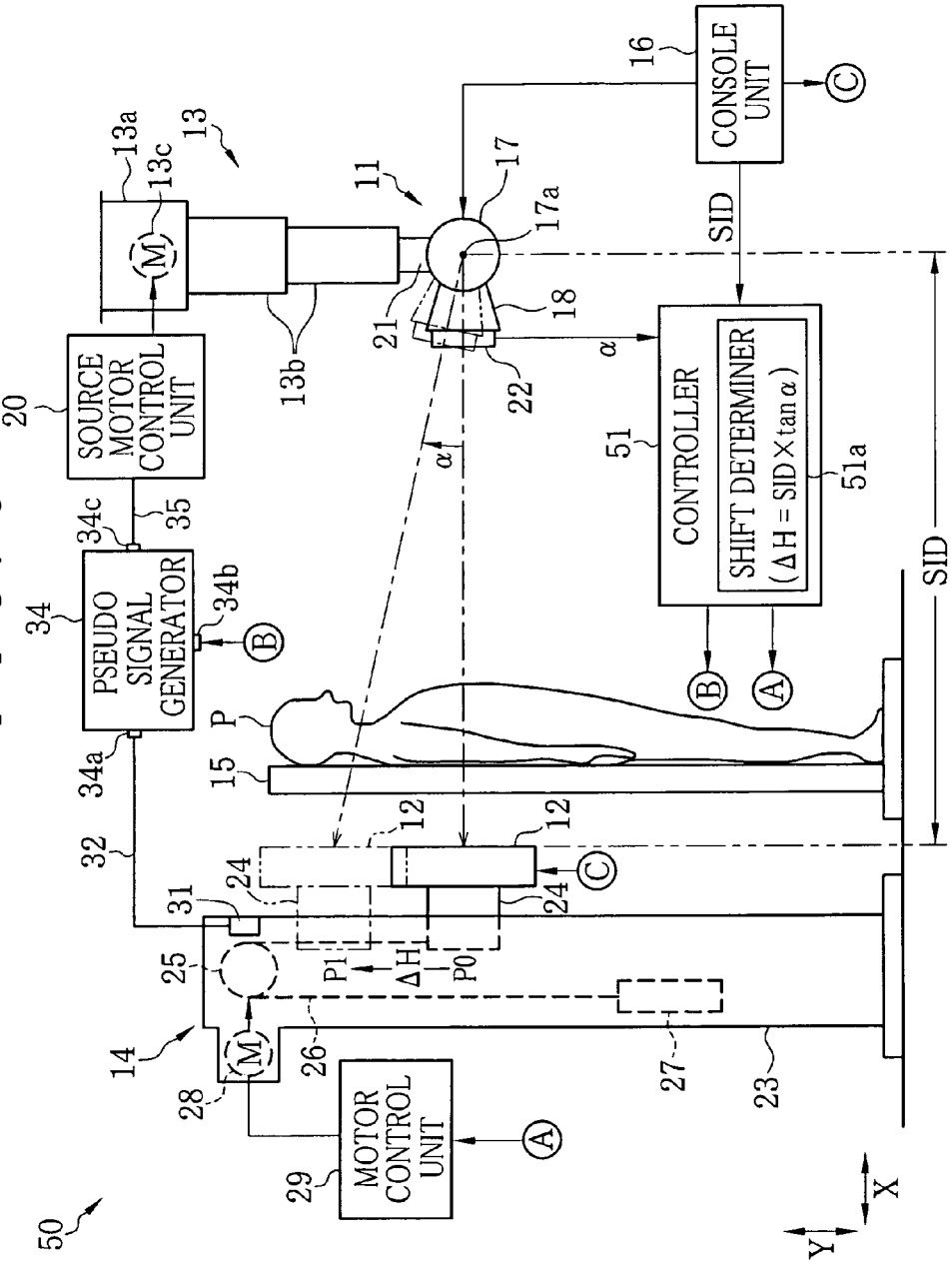
FIG. 5 is an explanatory view in a side elevation and a block diagram illustrating one preferred X ray imaging system in which a command signal is input manually.

In FIG. 5, an X ray imaging system 50 or radiation imaging system is illustrated. A controller 51 is constituted by a personal computer (PC) or the like for controlling the motor control unit 29 of the radiation detection apparatus 14. The motor control unit 29 is supplied by the controller 51 with a command signal for moving the FPD device 12 to a position designated through the console unit 16. For example, an imaging menu on the console unit 16 is utilized to designate a region of interest in the body of the patient P.

A shift determiner 51a for a shift amount in the controller 51 is similar to that of the first embodiment. For this element, a control program is modified suitably. The controller 51 is connected to the angle detector 22 by use of a communication port or the like. If the orientation angle of the X ray source 11 is changed by an operator, the angle detector 22 supplies the controller 51 with angle information of the orientation angle α of the X ray source 11. In the controller 51, the shift determiner 51a calculates the shift amount ΔH of the FPD device 12 corresponding to the orientation angle α of the X ray source 11. A command signal is input to the motor control unit 29 according to the shift amount ΔH.

For the X ray imaging system 50, the first embodiment of the X ray imaging system 10 is repeated except for the absence of the elevation switch 30 in the radiation detection apparatus 14. Also, the operation of the X ray imaging system 10 is repeated for the X ray imaging system 50.

[3rd Embodiment]

Figure 6:
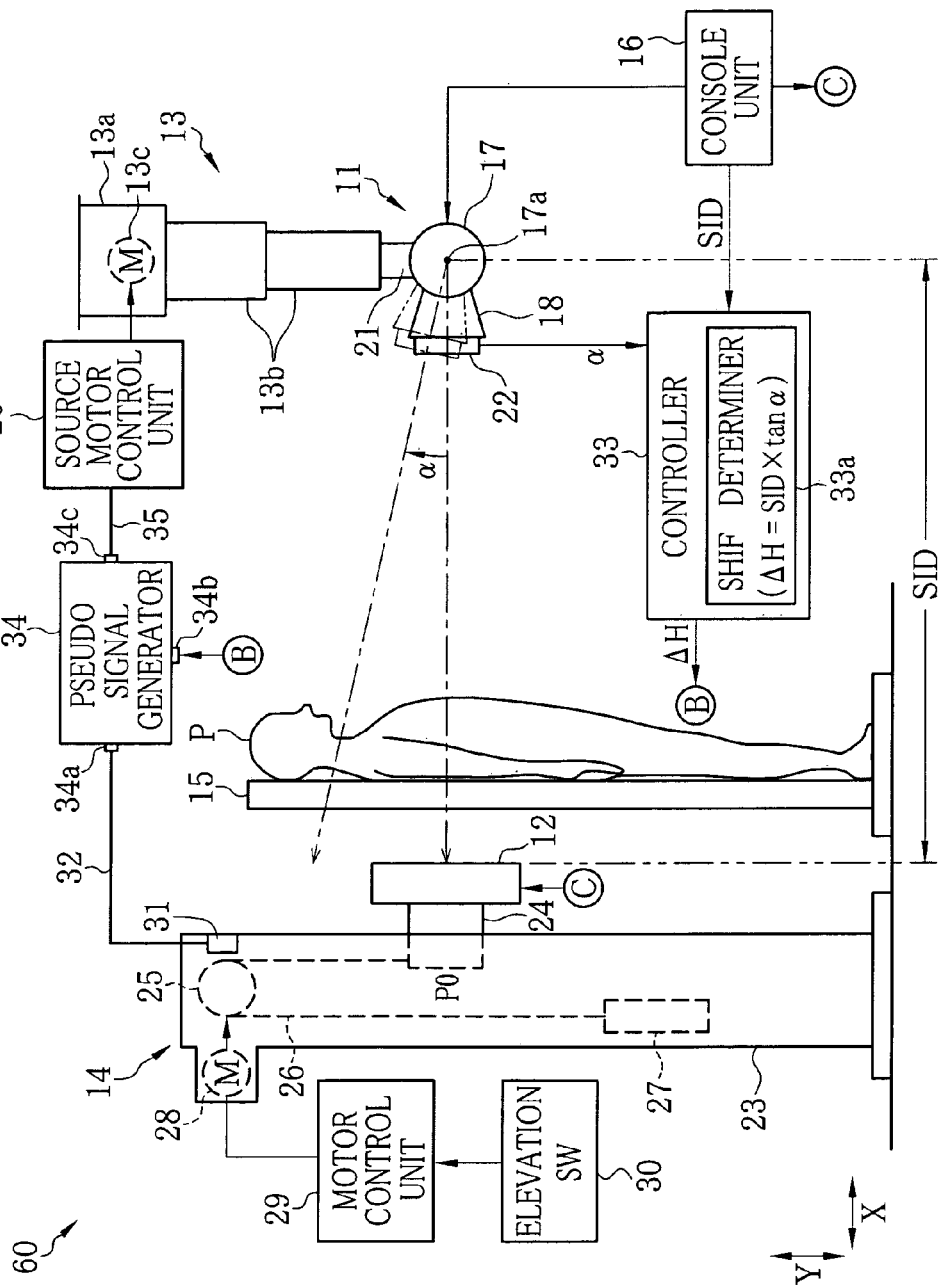
FIG. 6 is an explanatory view in a side elevation and a block diagram illustrating another preferred X ray imaging system in which an X ray source is moved manually.

In FIG. 6, an X ray imaging system 60 or radiation imaging system is illustrated. The X ray imaging system 10 is repeated with a difference in that the controller 33 is not connected with the motor control unit 29 in the radiation detection apparatus 14 in the X ray imaging system 60.

If the direction of the X ray source 11 is changed in the X ray imaging system 60, the motor control unit 29 is not supplied with the shift amount ΔH from the shift determiner 33a of the controller 33, so that the FPD device 12 does not move. In a manner similar to the first embodiment, the signal of the shift amount ΔH is input to the pseudo signal generator 34.

Figure 7:
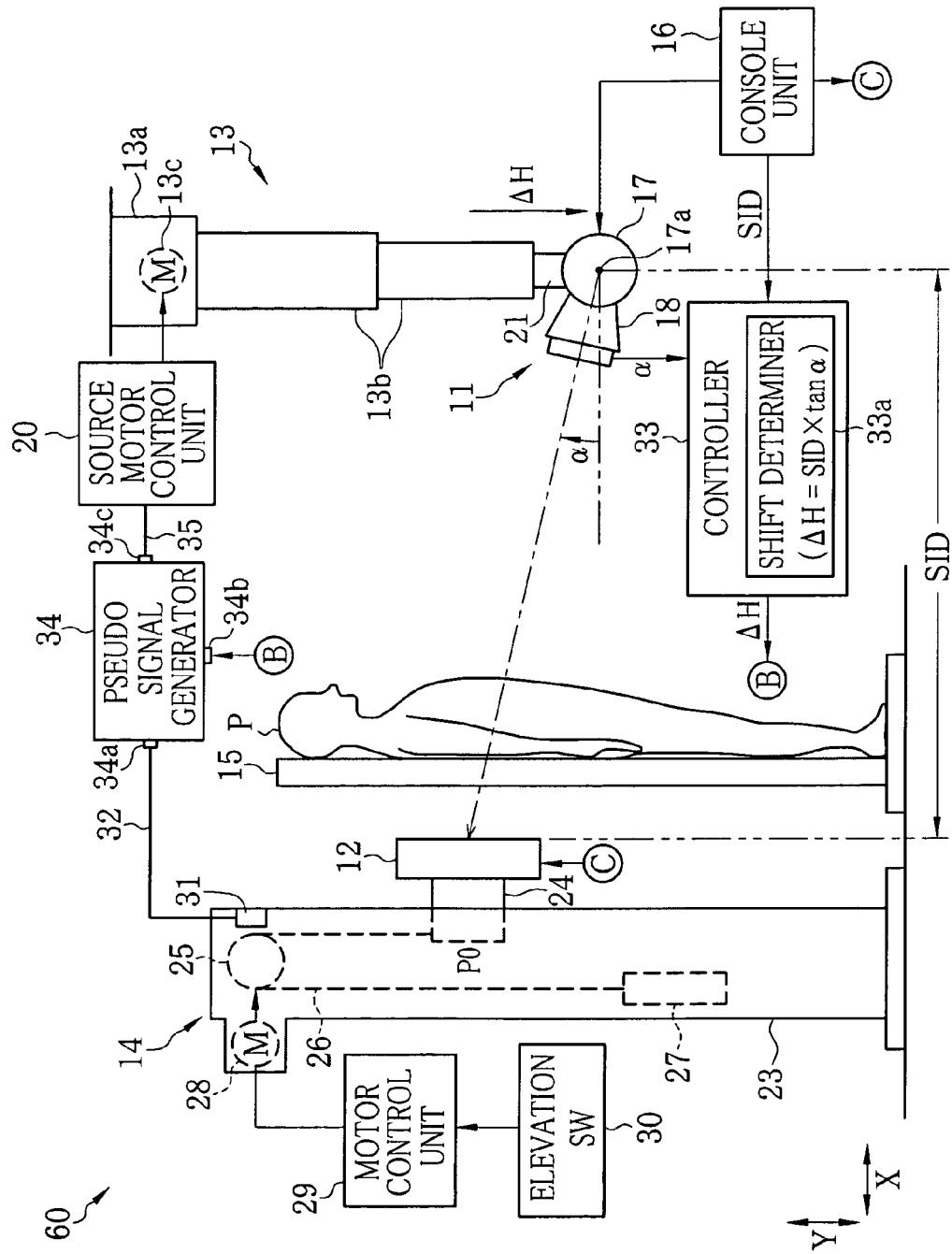
FIG. 7 is an explanatory view in a side elevation and a block diagram illustrating the same as FIG. 6 but in which the X ray source is moved down.

In the present embodiment, the FPD device 12 does not move even if the direction of the X ray source 11 changes. The voltage input by the potentiometer 31 to the pseudo signal generator 34 is unchanged. In the pseudo signal generator 34, the voltage in association with the shift amount ΔH is subtracted from the voltage of the potentiometer 31 as signal values. If the X ray source 11 is rotated by the angle α upwards, then a pseudo signal, which corresponds to a position lower than a position P0 of the FPD device 12 by the shift amount ΔH, is input to the source motor control unit 20 in the radiation apparatus 13. As a result, the X ray source 11 is moved downwards by the shift amount ΔH. See FIG. 7. X rays emitted by the X ray source 11 travel with an inclination of the angle α with respect to a normal line of the detector surface.

Thus, it is possible to change the orientation angle of the X ray source 11 relative to the FPD device 12 by pivotally moving the X ray source 11 manually. The FPD device 12 can remain without shift.

Also, the feature of the third preferred embodiment may be added to the radiation imaging system of the first preferred embodiment. In a normal mode, the FPD device 12 is shifted up or down at the obtained shift amount when the X ray source 11 is pivotally moved. A specific mode is set in a predetermined condition of the operation. In the specific mode, the FPD device 12 is kept without shift. The X ray source 11 is pivotally moved and also shifted up or down at the obtained shift amount, so that the FPD device 12 can become located on a straight line extending in a forward direction of the X ray source 11. Note that the predetermined condition can be a condition of testing before first use of the radiation imaging, condition before or after the system inspection, and condition of emergency operation upon occurrence of an error of the system.

[4th Embodiment]

Figure 8:
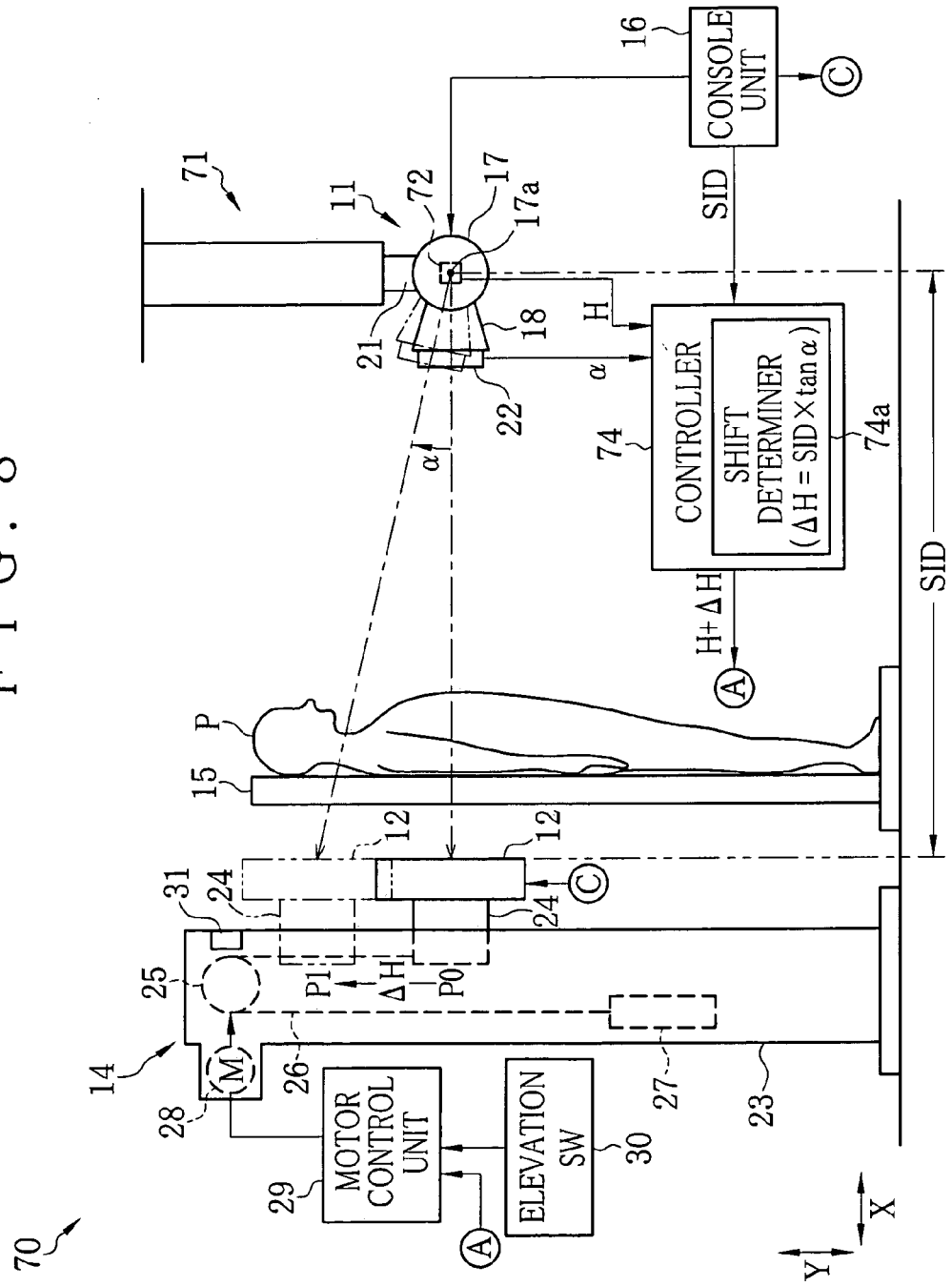
FIG. 8 is an explanatory view in a side elevation and a block diagram illustrating still another preferred X ray imaging system in which a height of the FPD device is changed.

In FIG. 8, an X ray imaging system 70 or radiation imaging system is illustrated. A radiation apparatus 71 having a support device as a second moving device does not have a mechanism for vertically moving the X ray source 11. There is no connection of a signal line or cable from the potentiometer 31 of the radiation detection apparatus 14. In the fourth embodiment, the X ray imaging system 70 does not have an auto tracking function, and enables long region imaging with a rotational motion mechanism.

In the embodiment, a height sensor 72 is secured to for measuring a height of the pivot axis 17*a* from the floor surface by use of laser, ultrasonic wave or the like. A controller 74 is connected to the height sensor 72 by a signal line or the like. The controller 74 operates according to the height H detected by the height sensor 72, and controls the motor control unit 29 of the radiation detection apparatus 14 to set the height of the FPD device 12 equal to that of the X ray source 11. A shift determiner 74*a* calculates a shift amount ΔH. If the direction of the X ray source 11 is changed, then the controller 74 controls the motor control unit 29 according to a sum of the height H and the shift amount ΔH from the shift determiner 74*a*. The FPD device 12 is moved to a position on a straight line extending in a forward direction of the X ray source 11.

Consequently, the long region imaging of image stitching is possible with a rotational motion mechanism even in the X ray imaging system without an auto tracking function, because the height sensor 72 is operated.

[5th Embodiment]

Figure 9:
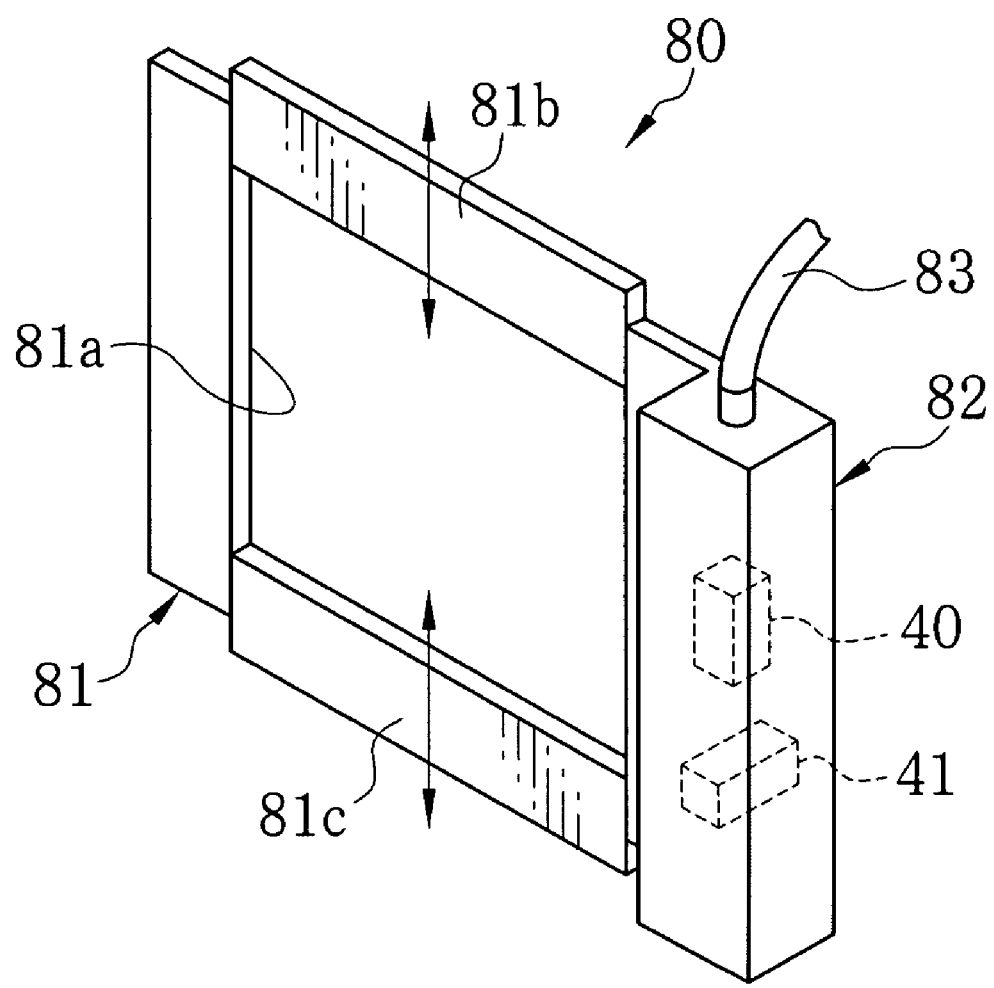
FIG. 9 is a perspective view illustrating one preferred angle detector of which a collimator has adjustable plates.

An example of angle detector 80 is provided. In FIG. 9, the angle detector 80 includes a detector frame 81, a detector housing 82 and a signal line or cable 83. The detector frame 81 is a portion for mounting on the filter rails 18*b* of the collimator 18. The detector housing 82 contains the angle sensors 40 and 41. The signal line 83 is connected for outputting angle information. The detector housing 82 and the signal line 83 are the same as those of the first embodiment.

An aperture 81*a* is formed in the detector frame 81. Adjustable plates 81*b* and 81*c* are arranged so that the aperture 81*a* is defined between those, and are movable up and down discretely. The adjustable plates 81*b* and 81*c* are manually moved to adjust a size of the detector frame 81 in a vertical direction, for example within a range of 140-170 mm.

The collimator 18 as a beam limiting device is provided by various manufacturers. An interval between the filter rails 18*b* may differ between those. However, the interval can be changed by the position adjustment of the adjustable plates 81*b* and 81*c* in the angle detector 80 of the embodiment. The angle detector 80 can be mounted on the filter rails 18*b* of any of the manufacturers.

[6th Embodiment]

Another preferred angle detector 90 is provided. In FIG. 10, the angle detector 90 is settable on the filter rails 18*b* of the collimator 18 similarly to the above embodiments. A first ultrasonic receiver 91*a* and a second ultrasonic receiver 91*b* are incorporated in the angle detector 90 in place of the acceleration sensors. The second ultrasonic receiver 91*b* is symmetric to the first ultrasonic receiver 91*a* in the vertical direction. An ultrasonic transmitter 92 is positioned on a lateral surface of the FPD device 12, emits ultrasonic waves, which are received by the ultrasonic receivers 91*a* and 91*b*. A combination of the ultrasonic receivers 91*a* and 91*b* is adapted to measure a distance from the ultrasonic transmitter 92. Note that a belt or other fastening element is used to secure the ultrasonic transmitter 92 to the FPD device 12 removably at its center portion with respect to the vertical direction.

A controller 93 is connected to the angle detector 90 by a signal line or the like. Distance information is input from the angle detector 90 to the controller 93 for a distance L1 from the ultrasonic transmitter 92 to the first ultrasonic receiver 91*a* and a distance L2 from the ultrasonic transmitter 92 to the second ultrasonic receiver 91*b*. The controller 93 includes an angle determiner 94 and a shift determiner 95. The angle determiner 94 calculates the angle of the X ray source 11 according to the distance information L1 and L2. The shift determiner 95 calculates the shift amount ΔH for moving the FPD device 12 according to the angle calculated by the angle determiner 94.

The angle determiner 94 calculates the orientation angle α of the X ray source 11 according to the fact that the distances L1 and L2 are equal if the direction of the X ray source 11 is horizontal and are different from one another if the X ray source is directed differently. The shift determiner 95 is constructed equally to that of the above embodiments, and calculates the shift amount ΔH according to Equation 1, and inputs a signal of the shift amount ΔH to the motor control unit 29 and the pseudo signal generator 34 in the radiation detection apparatus 14.

In short, the angle detector 90 detects the angle of the X ray source 11 by use of the ultrasonic transmitter 92 on the FPD device 12. Furthermore, the angle determiner 94 can be incorporated in the angle detector 90. It is not necessary to determine the angle α itself for position control of the FPD device 12 upon changing the angle of the X ray source 11. The motor control unit 29 can be controlled to set the FPD device 12 in a position for setting the distance L2 equal to the distance L1.

In the above embodiments, the FPD device 12 as a radiation detection device is moved up and down relative to the body of the patient in the upright posture. However, an FPD device in the invention may be moved horizontally relative to the body of the patient in the supine posture. Furthermore, an FPD device can be moved straight in parallel with a detector surface for two-dimensional imaging for the body.

The radiation imaging of the invention may be any type of non destructive inspection of an object in the medical field by use of radiation. The radiation in the invention may be other radiation than X rays, for example, gamma radiation, infrared radiation and the like.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An assist apparatus for a radiation imaging system including a radiation source for applying radiation to a body, a radiation detection device, opposed to said radiation source, for detecting said radiation transmitted through said body, to produce an image, a first moving device for moving said radiation detection device on a path parallel with a detector surface thereof, a shift detector for detecting a position of said radiation detection device, a second moving device for moving said radiation source linearly according to a detection signal from said shift detector, to follow movement of said radiation detection device, a rotational support device for supporting said radiation source in a rotatable manner about an axis, to adjust an orientation angle thereof, said assist apparatus comprising:

an angle detector, disposed on said radiation source removably, for detecting said orientation angle;

a shift determiner for operating when said radiation source is moved pivotally with said rotational support device, and for determining a shift amount for shifting said radiation detection device to a position opposed to said radiation source according to said orientation angle from said angle detector and a distance between said radiation source and said radiation detection device; and a pseudo signal generator for generating a pseudo signal of a level irrespective of said shift amount by correcting said detection signal from said shift detector according to said shift amount from said shift determiner, and for supplying said second moving device with said pseudo signal.

2. An assist apparatus as defined in claim 1, wherein said radiation source includes:

a beam limiting device for limiting a field of said radiation;

a pair of filter rails, disposed on said beam limiting device, for securing of an additional filter for changing a characteristic of said radiation;

said angle detector includes a detector portion retained on said filter rails.

3. An assist apparatus as defined in claim 2, wherein said detector portion has a size variable in association with an interval between said filter rails.

4. An assist apparatus as defined in claim 1, wherein said angle detector includes an acceleration sensor for detecting said orientation angle.

5. An assist apparatus as defined in claim 1, wherein said angle detector includes two one-axis acceleration sensors arranged so that axial directions thereof are substantially perpendicular to one another;

said shift determiner selects information of said orientation angle from one of said one-axis acceleration sensors having a higher angular resolution, to determine said shift amount.

6. An assist apparatus as defined in claim 1, wherein said pseudo signal generator generates said pseudo signal by subtracting a signal value of said shift amount from a signal value of said position of said radiation detection device.

7. An assist apparatus as defined in claim 1, wherein said shift detector is constituted by a potentiometer.

8. An assist apparatus as defined in claim 7, wherein said angle detector includes a radio transmitter for transmitting information of said detected orientation angle to said shift determiner.

9. An assist apparatus as defined in claim 7, wherein said angle detector includes:

two ultrasonic receivers for receiving an ultrasonic wave from an ultrasonic transmitter positioned on said radiation detection device, to measure distances from said ultrasonic transmitter;

an angle determiner for determining said orientation angle according to said distances measured by said ultrasonic receivers.

10. An assist apparatus as defined in claim 1, wherein said shift amount has such a value as to move said radiation detection device on said path in a first direction defined according to a first rotational direction among two rotational directions of said radiation source with said first moving device when said radiation source is pivotally moved in said first rotational direction.

11. An assist apparatus as defined in claim 1, wherein said radiation source is movable linearly in a first direction and a second direction reverse thereto with said second moving device;

when said radiation source is pivotally moved in a first rotational direction defined according to said first direction, said second moving device moves said radiation source in said second direction.

12. An assist apparatus as defined in claim 1, wherein said radiation detection device is an FPD device.

13. An assist apparatus as defined in claim 1, wherein said radiation is X rays.

14. A radiation imaging system comprising:

a radiation source for applying radiation to a body;

a radiation detection device, opposed to said radiation source, for detecting said radiation transmitted through said body, to produce an image;

a first moving device for moving said radiation detection device on a path parallel with a detector surface thereof;

a shift detector for detecting a position of said radiation detection device;

a second moving device for moving said radiation source linearly according to a detection signal from said shift detector, to follow movement of said radiation detection device;

a rotational support device for supporting said radiation source in a rotatable manner about an axis, to adjust an orientation angle thereof;

an angle detector, disposed on said radiation source removably, for detecting said orientation angle;

a shift determiner for operating when said radiation source is moved pivotally with said rotational support device, and for determining a shift amount for shifting said radiation detection device to a position opposed to said radiation source according to said orientation angle from said angle detector and a distance between said radiation source and said radiation detection device;

a pseudo signal generator for generating a pseudo signal of a level irrespective of said shift amount by correcting said detection signal from said shift detector according to said shift amount from said shift determiner, and for supplying said second moving device with said pseudo signal; and a controller for controlling said first moving device according to said shift amount from said shift determiner.

15. A radiation imaging system comprising:

a radiation source for applying radiation to a body;

a radiation detection device, opposed to said radiation source, for detecting said radiation transmitted through said body, to produce an image;

a first moving device for moving said radiation detection device on a path parallel with a detector surface thereof;

a shift detector for detecting a position of said radiation detection device;

a second moving device for moving said radiation source linearly according to a detection signal from said shift detector, to follow movement of said radiation detection device;

a rotational support device for supporting said radiation source in a rotatable manner about an axis, to adjust an orientation angle thereof;

an angle detector, disposed on said radiation source removably, for detecting said orientation angle;

a shift determiner for operating when said radiation source is moved pivotally with said rotational support device, and for determining a shift amount for shifting said radiation detection device to a position opposed to said radiation source according to said orientation angle from said angle detector and a distance between said radiation source and said radiation detection device; and a pseudo signal generator for generating a pseudo signal by subtracting a signal value of said shift amount from a signal value of said position according to said shift amount from said shift determiner, and for supplying said second moving device with said pseudo signal.

* * * * *